's Patent [19]

[11] 4,361,528
[45] Nov. 30, 1982

Ginsburg et al.

[54] METHOD OF MAKING THERMOPLASTIC DENTAL IMPRESSION TRAY

[75] Inventors: Stephen J. Ginsburg, Ann Arbor; Frederick E. Draheim, Milford, both of Mich.

[73] Assignee: Black Knight Investments Limited, Georgetown, Cayman Islands

[21] Appl. No.: 71,214

[22] Filed: Aug. 30, 1979

[51] Int. Cl.³ .................. A61C 3/00; B29C 3/00
[52] U.S. Cl. ........................ 264/28; 264/16; 264/168; 264/157; 264/162
[58] Field of Search .............. 264/16, 17, 161, 162, 264/138, 28, 348, 157, 69; 433/37, 48, 171; 260/31.8 M, 31.8 R, 31.8 C; 51/164.5, 313; 525/302

[56] References Cited

U.S. PATENT DOCUMENTS

| | | | |
|---|---|---|---|
| 1,955,709 | 4/1934 | Kinsley | 433/200 |
| 2,013,295 | 9/1935 | Tidd | 264/17 |
| 2,069,983 | 2/1937 | Ubben | 260/31.8 M |
| 2,234,993 | 3/1941 | Vernon et al. | 264/16 |
| 2,341,593 | 2/1944 | Burkhardt et al. | 264/16 |
| 2,558,139 | 6/1951 | Knock et al. | 264/16 |
| 2,685,134 | 8/1954 | Thompson | 433/48 |
| 2,848,750 | 8/1958 | Sanneke et al. | 264/17 |
| 2,944,293 | 7/1960 | Taylor | 264/17 |
| 3,473,225 | 10/1969 | Deuschle et al. | 433/48 |
| 3,654,703 | 4/1972 | McAdoo | 433/48 |
| 3,684,466 | 8/1972 | Petrone | 51/313 |
| 3,758,642 | 9/1973 | Logemann et al. | 260/31.8 M |
| 3,823,205 | 7/1974 | Zimmt | 260/31.8 M |
| 3,936,403 | 2/1976 | Sakaguchi et al. | 260/31.8 M |
| 4,161,065 | 7/1979 | Gigante | 433/37 |
| 4,227,877 | 10/1980 | Tureaud et al. | 433/37 |
| 4,247,287 | 1/1981 | Gigante | 433/37 |

OTHER PUBLICATIONS

Peyton et al., "Restorative Dental Materials", Mosby, St. Louis, (1971), pp. 452–455, 458, 462 and 484.
Randolph et al., "Plastics Engineering Handbook", Reinhold, N.Y., (1960), pp. 445 and 446.
Tylman et al., "Acrylics and Other Synthetic Resins in Dentistry", Lippincott, Phila., (1947), pp. 311, 330 and 331.
Skinner et al., "Science of Dental Materials", Saunders, Phila., (1968), pp. 11/166, 11/166, 12/179–12/183, 12/185, 208/13, 210/13.

Primary Examiner—Willard E. Hoag
Attorney, Agent, or Firm—Sherman & Shalloway

[57] ABSTRACT

A method of making a thermoplastic dental impression tray which can be heated, placed into the patient's mouth where it can be intimately molded to approximate the patient's tissues and characterized in that the tray will maintain its molded structure to a high degree of accuracy. Methyl methacrylate monomer liquid and polymer powder are mixed together and the mixture is allowed to reach a doughy state. The mixture is placed into a mold conforming to the desired structure of the tray. The mold is then heated for a sufficient time under pressure to polymerize the monomer to provide a tray characterized in that when heated to above 135° F. it will become soft enough so that it can be placed into the patient's mouth for intimate molding therein and which will become so hard when cooled in the mouth that it will exhibit a recovery rate of less than 2% after removal from the mouth so that the precision of the impression is accurately maintained.

15 Claims, 2 Drawing Figures

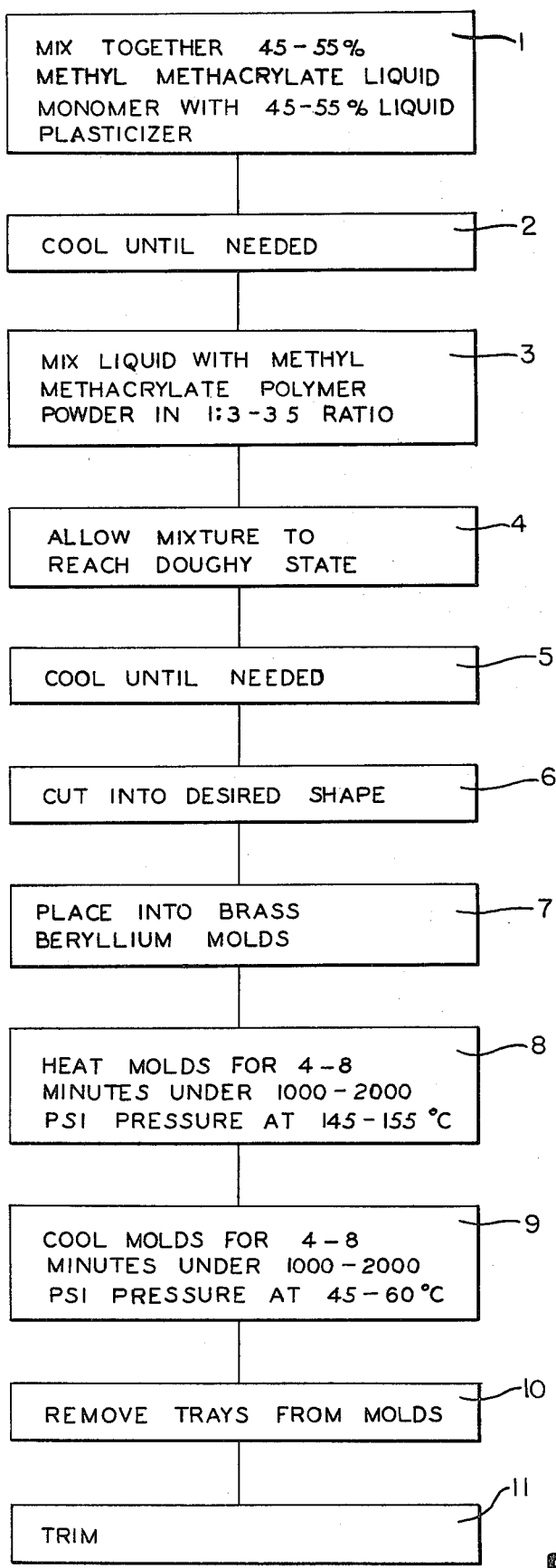
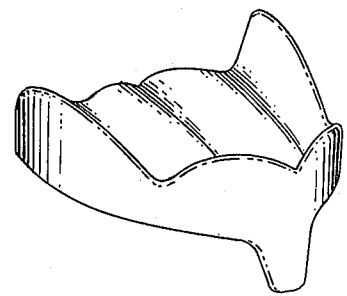
FIG. 2
FIG. 1

METHOD OF MAKING THERMOPLASTIC DENTAL IMPRESSION TRAY

BACKGROUND OF THE INVENTION

This invention relates to thermoplastic dental impression trays. More particularly, it involves a method of making a thermoplastic dental impression tray which maintains its molded structure to a high degree of accuracy.

To form a final impression of a dentulous or edentulous alveolar ridge, in the course of producing a male model of desired oral tissues, conventional practice involves the use of commercially available preliminary impression trays of use with either the maxillary or the manibular alveolar ridges and contiguous tissues, in either dentulous or edentulous cases. These trays are available in a range of sizes so that one which makes an approximate fit with the patient's mouth area may be chosen for use. They have a cross-section characterized by a base with two normally extending walls so that they will surround the ridge of which an impression is to be formed. These stock trays are typically formed of aluminum or other material that may be bent or trimmed at the edges to provide the fit for an individual patient. Impression material is placed in the tray and a female cast of the required area is formed. This cast is then typically used to form a male model of the patient's mouth section either in the dental office or in a separate dental laboratory. The laboratory or dental office then uses this male model to form a custom final impression tray out of a plastic material which closely conforms to the individual patient's oral cavity. The thus formed custom molded tray is then shipped back to the dental practitioner to use the custom tray to form a final impression of the required area by placing a high definition, settable, impression material such as alginate, silicone, or polysulfide or the like, into the impression tray. The tray is then pressed to cause the impression material to closely surround the desired area. As known in the art, it is necessary that the spacing between the tray and the tissues must be on the order of only several millimeters to obtain an accurate final impression. Since the custom tray already anatomically conforms to the patient's tissues, it is generally not subject to any further deformation.

It can be seen that this conventional practice typically requires two procedures and is relatively expensive. Additionally, the stock impression trays may cause discomfort to the patient because of its relatively gross fit. Similarly, inaccuracies creep into the procedure because of the multiple transfer steps.

A number of alternative means for forming final impressions have been proposed to overcome these recognized inaccuracies of the conventional procedure. For example, several forms of stock trays have been devised which may be shaped exteriorly of the mouth to improve the accuracy of the initial impressions. U.S. Pat. No. 3,473,225 to Deuschle et al discloses such a stock tray which is formed of a thermoplastic material which can be molded outside of the mouth by the dentist after slight heating in order to improve its fit. Similarly, U.S. Pat. No. 3,653,705 to McAdoo discloses a thermoplastic dental impression tray which may be cut and then stapled back together in order to better conform to the patient's mouth.

Several arrangements have been proposed for elimination of the initial impressions altogether and formation of a final custom impression tray directly in the patient's mouth. U.S. Pat. No. 1,995,709 to Kinsley discloses an impression tray formed of a woven metal matrix with a soft pliable covering that may be contoured directly to the patient's mouth. German Pat. Nos. 715,041 and 1,297,811 are representative of the use of thermoplastic materials in the form of dental impression trays and the like. In German Pat. No. 715,041 there is disclosed a dental impression tray which can be heated by placing it in boiling water so that it can be bent in accordance with the mouth proportions. However, this and other prior art attempts to solve the problems associated with conventional processing all have one fatal flaw: after they have been molded, they do not retain their molded structure to a sufficient degree of accuracy. Once they have been deformed they have a tendency to return to their original shape. This tendency is referred to as memory or recovery rate. It is evident that if the memory of the tray is such that it has a tendency to return to its original shape, the accuracy of the impression is impaired rendering it almost totally useless. For this reason, commercial acceptance of these known thermoplastic impression trays have not been forthcoming.

It is believed that the prior art devices have not been acceptable because their glass transition temperatures were too low. The term "glass transition temperature" is the temperature at which a thermoplastic material changes from a glassy brittle state to a rubbery state characterized by a change in stiffness of several orders of magnitude. In this rubbery state, the thermoplastic material may possess relatively stiff properties. However, it will still have too high a recovery rate for commercial acceptability.

SUMMARY OF THE INVENTION

Therefore, it is the primary object of this invention to provide a method for making a thermoplastic dental impression tray which can be molded in the mouth of the patient, yet maintain the molded structure with a high degree of accuracy.

It is a further object of this invention to provide a dental impression tray such as described as above in an economical and efficient manner lending itself to a mass production environment.

Briefly, the objects and advantages of the present invention are accomplished by mixing together a methyl methacrylate monomer liquid and methyl methacrylate polymer powder. Preferably, the liquid monomer is mixed with a liquid plasticizer. In the preferred embodiment, the liquids are mixed together in the ratio of 45–55% by weight of methyl methacrylate monomer and 45–55% by weight of plasticizer, preferably Diethyl Phthlate. According to one feature of this invention, the polymer powder to liquid ratio is about 3–3.5 to 1 parts by weight. In order to obtain the intimate mixture of powder and liquid together in a relatively short time, the liquid monomer is cooled to a temperature below about 0° F. before mixing it with the powder. After the mixture has reached a doughy state, it is placed into a mold conforming to the desired structure of the tray. The mold is then heated for a sufficient time under pressure to polymerize the monomer to provide a tray characterized in that it can be heated above 135° F., placed in the patient's mouth wherein it can be molded to conform to the patient's tissues, and which will be-come so hard after cooling in the mouth that it will maintain the molded structure to a high degree of accuracy defined by a recovery rate of less than 2% after the molded tray has been removed from the patient's mouth. Pursuant to still another feature of this invention, the mold is heated to between 145°-155° C. at about 1000-2000 psi pressure for only 4-8 minutes, as compared with conventional thermoplastic processing techniques used in the dental industry in which the molding process lasts between 1½ to 2½ hours.

BRIEF DESCRIPTION OF THE DRAWINGS

These and other objects and advantages of the present invention will become apparent upon reading the following specification and by reference to the drawings in which:

FIG. 1 is a flow chart illustrating the processing steps in practicing the preferred embodiment of the method of this invention; and FIG. 2 is a perspective view showing an example of a thermoplastic dental impression tray made in accordance with this invention.

DESCRIPTION OF THE PREFERRED EMBODIMENT

The first step in the process is to mix together a methyl methacrylate monomer liquid and a suitable plasticizer to form a liquid blend as represented by box 1 in the flow chart of FIG. 1. Preferably, the liquid blend includes 45-55% parts by weight of a non-crosslinked methyl methacrylate monomer and 45-55% by weight of a plasticizer. A suitable methyl methacrylate monomer is that sold by Esschem Company, a Division of Sartomer Industries, Inc., P.O. Box 56, Essington, Pa. 19029 as stock number 901 S 0000. The specific properties of this material are set forth in Table I.

TABLE 1

| Manufacturer's Identification Name: | Methyl Methacrylate Monomer Stock Number 901 S 0000 | |
|---|---|---|
| Composition: | Methyl Methacrylate monomer. Contains 60 ppm hydroquinone to prevent premature polymerization | |
| Specification: | | Test Method |
| Assay, % | 99.8 | Gas Chromatograph |
| Acidity as methacrylic acid, % | 0.005 max. | Titration |
| Color | 10 max. | APHA |
| HQ, ppm | 60 ± 10 | n-Butylamine, UV Spectrophotometer |
| Refractive Index @ 25° C. | 1.412 ± 0.001 | Refractometer |
| Specific Gravity @ 25° C. | 0.936 ± 0.001 | Hydrometer |
| Water, % | 0.05 | Karl Fischer, Aquatest |

A suitable example of the plasticizer is stock No. 927 S 0000 from the same company. More than about 55% parts by weight of plasticizer gives the tray too high a memory or recovery rate, whereas less than 45% of parts by weight makes the tray too stiff for easy moldability in the mouth of the patient after heating it to above 135° F. 52% parts by weight of plasticizer and 48% parts by weight of the non-crosslinked monomer has provided excellent results. Preferably, the plasticizer is diethyl phthalate in liquid form, the specific properties of which are set forth in Table II.

TABLE II

| Manufacturer's Identification Name: | Soft Curing Liquid Stock Number 927 S 0000 | |
|---|---|---|

TABLE II-continued

| Composition: | Plasticizer, Diethyl Phthalate | |
|---|---|---|
| Specification: | | Test Method |
| Appearance | Clear, colorless liquid | Visual Check |
| Refractive Index @ 25° C. | 1.501 ± 0.001 | Refractometer |
| Specific Gravity @ 25° C. | 1.120 ± 0.005 | Hydrometer |
| Identity | Match standard spectra | Infrared |
| Purity | No impurities | Gas Chromatograph |

The appropriate amounts of each liquid are weighed and then poured together into a beaker or other container.

According to a feature of this invention represented by box 2, the container holding the liquid blend is then cooled to below 0° F. Preferably, the container holding the monomer liquid is placed in a cooler set at a temperature of −10° F. for a period long enough for the monomer to reach about this temperature. Even at this temperature the monomer remains in a liquid state. This cooling serves two functions. First, from a production standpoint, a large quantity of liquid blend can be made at one time and stored in the cooler almost indefinitely until need for use in production. Secondly, and more importantly, the cold liquid monomer allows more of the methyl methacrylate polymer to be mixed with the liquid than would otherwise be attainable. Use of standard processing techniques calls for a 2:1 parts by weight mixture of polymer to monomer. However, we have found it preferable to use 3-3.5 parts by weight polymer powder to 1 part by weight liquid monomer. The increased amount of polymer powder gives the resultant device a high stability and a more brittle structure, resulting in a low recovery rate.

In step 3, the liquid monomer is removed from the cooler and poured into a bowl along with the previously weighed polymer powder. An acceptable methyl methacrylate polymer powder is Type 139 Standard Denture Polymer sold by the aforementioned Esschem Company. The specifies of this preferred material is set forth in Table III.

TABLE III

| Manufacturer's Identification Name: | Polymer Type 139 Fibered Stock Number 031 B 1602 | |
|---|---|---|
| Composition: | Consists of a blend of the following polymers: | |
| | A. Polymethyl methacrylate having a molecular weight of approximately 900,000. | |
| | B. Copolymer, resulting from the polymerization of a mixture of methyl methacrylate monomer, ethyl acrylate monomer and dibutyl phthalate. | |
| | C. Copolymer resulting from the polymerization of a mixture of methyl methacrylate monomer, butyl acrylate monomer and dibutyl phthalate. | |
| | The blend of polymers has a residual peroxide content of 0.2% to 0.3% and an average molecular weight of 650,000–800,000 calculated as methyl methacrylate polymer. | |
| | The particle size of the polymer blend, tested by dry screen analysis using standard test sieves is as follows: | |
| On 80 mesh | (0.0069) | 2% |
| On 100 mesh | (0.0058) | 1-5% |
| On 150 mesh | (0.0041) | 2-10% |
| On 250 mesh | (0.0024) | 20-50% |
| Thru 250 mesh | | 40-60% |

TABLE III-continued

The blend of polymers is pigmented using less than 0.2% inorganic pigments consisting of titanium dioxide, cadmium selnide, cadmium sulfide and iron oxide. Less than 0.3% rayon fibers are added to achieve desired shade and aesthetic appearance.

The mixture is then blended together by mixing it with a well-known blender, such as used in the bakery industry to blend dough, to intimately mix the powder with the liquid resulting in a viscous, yet pourable mixture. Due to the previous cooling of the liquid such a state can be achieved in about 2 minutes of blending. This mixture is then poured into a shallow pan, or cooky sheet, which, in this embodiment is approximately 15¼"×10¼"×¾".

Referring to step 4 of FIG. 1, this mixture is allowed to set to permit diffusion of the monomer into the polymer powder characterized by the mixture achieving a doughy like consistency. At room temperature, this state occurs in approximately 30-45 minutes. The pan can then be placed into the same cooler that was used to cool the liquid monomer blend (step 5), said cooler being kept at approximately −10° F. We have discovered that this mixture can be left almost indefinitely in the cooler until needed for further use. Accordingly, a large quantity of the dough-like material can be made at one time and stored until needed for further use. Of course, this is very advantageous in production environment.

When needed, the pan is removed from the cooler and the mixture is cut into the desired shape as represented by block 6 in FIG. 1. Typically, it is sliced into bars approximately ¼" wide and 3–5" long. The weight of such bars is between 0.03-0.04 lbs. depending upon the size of the tray being produced. The unused bar slices can be put back into the cooler and used at a later time as long as they are not left in room temperature for more than 10-15 minutes.

The next step as represented by step 7 in FIG. 1, is to place the cut strips or bars into the molds. The molds are preferably two pre-formed structures forming a U-shaped hollowed out portion when placed together, with such portion conforming to the desired structure of the tray as should be evident to one skilled in the art. The bars are laid into the bottom structure of the tray such that the bars generally conform to the U-shaped portion and the top structure of the tray is then alligned on top of the bottom structure. According to another feature of this invention, the molds are made of brass beryllium. We have discovered that this material is not only extremely durable, but it has excellent heat transfer characteristics that lends itself to an expeditious molding procedure as will now be described.

The eighth main step is to heat the mold under pressure in order to fully cure the methyl methacrylate. The molds are heated to a temperature range between 145°–155° C. at a pressure of about 1000-2000 psi applied between the opposite faces of the mold. A temperature higher than 155° C. has a tendency to cause the mixture to bubble, resulting in holes in the tray, whereas if the temperature is below 145° C., the tray will not cure properly and will be too soft for purposes of its intended use. A temperature of 150° C. and 1000 psi pressure has provided excellent results.

A very advantageous feature of this invention is that this curing process occurs between 4-8 minutes as compared to the 1½-2½ hour curing cycle used and recommended by the chemical manufacturers for curing acrylic materials used in dental applications. We have found that if the trays are cured for longer than about 8 minutes at this temperature and pressure, the tray will become too brittle and lose its moldability characteristics. On the other hand, if it is left in the hot press less than about 4 minutes, it will not cure properly and not give the device the rigid properties needed for its intended use. Preferably, the thermoplastic material is cured at about 150° C. for about 4½ minutes at about 1000 psi pressure.

In step 9, the trays can be removed from the hot press and allowed to cool to room temperature where the mold is opened and the resultant tray removed. Preferably, however, the mold is transferred to a cooling station in the machinery where cold water (approximately 45°–60° C.) is applied to the mold at about 1000-2000 psi pressure for a time period of 4-8 minutes. The purpose of this procedure is to bring the temperature of the tray to room temperature so that it can be handled during subsequent manufacturing processing. The range of times, temperatures, and pressures can be varied somewhat during this step. Cooling at 45°–60° C. for 4½ minutes at 1000 psi pressure has provided excellent results.

After the trays are removed (step 10) from the mold, they are trimmed to remove burrs and unwanted material from the tray structure, represented by box 11. A feature of this invention is that the trays are not hand trimmed, but instead they are placed into a vibrating receptacle containing thousands of small ceramic posts approximately ¼" in diameter and ½" long. The scrubbing action of the posts removes the burrs and polishes the tray to leave the finished device such as shown in FIG. 2. A wide variety of different tray configurations can be made according to this invention.

The device thus formed is characterized in that it becomes extremely moldable at temperatures above about 135° F. In a typical use of the tray, it is immersed in hot water (about 165° F.) for at least 2 minutes. The heated tray is then removed and centered on an existing arch form of the patient wherein the dentist molds the palate and flanges to closely approximate the peripheral tissues of the patient. The tray can be left in the patient's mouth to harden. The length of time will vary depending upon the size and thickness of the tray. In order to expedite the hardening process, the tray can be removed from the mouth and then chilled under cold tap water. The tray can then be re-inserted, with the dentist noting any areas of overextension. Such overextension can be trimmed with an acrylic burr, or the overextended flange portion may be selectively dipped in hot water and then trimmed with scissors. Any areas requiring further adaption may be selectively reheated and shaped. In any event, once the tray has been molded to its final configuration, it will maintain the molded structure to a high degree of accuracy. The tray made in accordance with this invention has exhibited recovery rates of less than 2%. Consequently, the dentist can proceed directly with making a final impression of the patient's oral anatomy without fear that the deformed tray will revert back to its original structure.

The tray made in accordance with this invention is believed to have a glass transition temperature above body temperature and below about 135° F. Consequently, the tray becomes moldable at temperatures low enough that the heated tray will not cause discomfort to the patient during the in-mouth procedure. More importantly, the tray will revert back to its glassy brittle state characterized by extreme rigidity when the device falls below its glass transition temperature while in the mouth of the patient, if left in the mouth long enough. In any event, we have found that the tray such as that shown in FIG. 2 will become hard eough after molding and remaining in the mouth of the patient for at least 15 minutes that it will withstand the forces applied to it by the dentist during removal such that it will have a recovery rate of less than 2%, and in most cases less than 1%, if it is directly placed under cold tap water for a period of at least 15 second by the dentist after removal. The percentage recovery rate is calculated by dividing the amount of movement of the tray after is is molded by the amount of deflection during molding. For example, if a portion of the tray is deflected 2 mm and the deflected portion moves 0.02 mm after deflection, the tray would be characterized by a recovery rate of 1%.

Therefore, it is now evident that the method described above not only provides a superior thermoplastic dental impression tray which exhibits an extremely low recovery rate, but that the present invention also provides a method of making such trays which is economical, relatively fast, and which readily lends itself to mass production. Therefore, while this invention as described in connection with certain specific examples thereof, no limitation is intended thereby except as defined in the appended claims.

The embodiments of the invention in which an exclusive property or privilege is claimed are defined as follows:

1. A method of making a thermoplastic dental impression tray which is capable of being molded in the mouth of a patient after reheating, said method comprising the steps of:
  (a) mixing 45-55% by weight of a methylmethacrylate liquid monomer and 45-55% by weight of a suitable liquid plasticizer to form a plasticized liquid monomer;
  (b) mixing said plasticized liquid monomer with methylymethacrylate polymer powder in a ratio of 1:3-3.5 parts by weight to form a mixture;
  (c) allowing the mixture to reach a doughy-like state;
  (d) placing said mixture into a mold conforming to the desired structure of the tray;
  (e) heating the mold at a temperature of about 145°-155° C. for about 4-8 minutes under pressure of about 1,000-2,000 p.s.i. to provide a tray that may be subsequently molded in the patient's mouth after heating it to above about 135° F., with the tray accurately maintaining its molded structure after removal from the mouth; and
  (f) removing the tray from the mold.

2. The method of claim 1 wherein the acrylic powder has an average molecular weight of at least 650,000.

3. The method of claim 1 which further comprises the step of:
  cooling the liquid blend to a temperature of below 0° F. before mixing said liquid with said polymer powder.

4. The method of claim 1 wherein said trays are trimmed by placing them in a vibrating bin filled with a plurality of ceramic posts.

5. The method of claim 1 wherein said mixture is poured into a shallow pan and allowed to reach a doughy-like state.

6. The method of claim 5 wherein said pan is cooled to below about 0° F. until needed for use.

7. The method of claim 5 wherein said mixture is sliced into bars weighing between 0.03-0.04 lbs.

8. The method of claim 1 wherein said molds are made of metal.

9. The method of claim 8 wherein said molds are heated at about 150° C. at about 1,000 psi pressure for about 4½ minutes.

10. The method of claim 8 wherein said molds are cooled to a temperature of about 45°-60° C. at a pressure of 1000 psi for about 4-8 minutes before the trays are removed.

11. A method of making a thermoplastic dental impression tray capable of being molded in the mouth of a patient after reheating, said method comprising the steps:
  a. blending not more than about 55% by weight of a non-crosslinked liquid methylmethacrylate monomer with not less than about 45% by weight of suitable liquid plasticizer in a container;
  b. placing the container in a cooler at a temperature of about −10° F.;
  c. mixing the liquid blend with a methlymethacrylate polymer powder in the ratio of about 3.5 parts by weight polymer powder to one part by weight of the liquid blend;
  d. pouring the mixture into a shallow pan;
  e. allowing the mixture to reach a doughy-like consistency;
  f. cutting the mixture into a plurality of bars weighing between 0.03-0.04 lbs.;
  g. placing a bar into a mold made of brass beryllium;
  h. heating the mold at a temperature of about 150° C. for about 4½ minutes at a pressure of about 1,000 psi to sufficiently polymerize the monomer to provide a tray that may be molded in a patient's mouth after heating to above 135° F., with the tray accurately maintaining its molded structure after removal from the mouth characterized by a recovery rate of less than about 2%;
  i. cooling the mold at a temperature of about 45°-60° C. at a pressure of about 1000 psi for about 4½ minutes; and
  j. removing the tray from the mold.

12. The method of claim 11 which further comprises the step of trimming the trays by placing them in a vibrating bin filled with a plurality of ceramic posts.

13. The method of claim 11 wherein said plasticizer is diethyl phthalate.

14. The method of claim 11 wherein said polymer powder is a blend of (a) polymethyl methacrylate, (b) a first copolymer resulting from the polymerization of a mixture of methyl methacrylate monomer, ethyl acrylate monomer, and dibutyl phthalate, and (c) a second copolymer resulting from the polymerization of a mixture of methyl methacrylate monomer, butyl acrylate monomer, and dibutyl phthalate.

15. The method of claim 11 wherein the methyl methacrylate polymer has an average molecular weight of at least 650,000.

* * * * *